US009265826B2

(12) United States Patent
Crocker et al.

(10) Patent No.: US 9,265,826 B2
(45) Date of Patent: *Feb. 23, 2016

(54) SIGLEC-9 BINDING AGENTS

(71) Applicant: University Court of the University of Dundee, Dundee, Scotland (GB)

(72) Inventors: Paul Richard Crocker, Dundee (GB); Bjoern Biedermann, Dundee (GB); David Bowen, Leeds (GB)

(73) Assignee: University Court of the University of Dundee, Dundee (GB)

( * ) Notice: Subject to any disclaimer, the term of this patent is extended or adjusted under 35 U.S.C. 154(b) by 57 days.

This patent is subject to a terminal disclaimer.

(21) Appl. No.: 13/796,958

(22) Filed: Mar. 12, 2013

(65) Prior Publication Data

US 2013/0302317 A1 Nov. 14, 2013
US 2016/0000908 A9 Jan. 7, 2016

Related U.S. Application Data

(60) Continuation of application No. 12/884,120, filed on Sep. 16, 2010, now Pat. No. 8,394,382, which is a division of application No. 12/091,749, filed as application No. PCT/GB2006/003983 on Oct. 27, 2006, now abandoned.

(30) Foreign Application Priority Data

Oct. 28, 2005 (EP) .................................. GB0521991

(51) Int. Cl.
| | |
|---|---|
| *A61K 39/395* | (2006.01) |
| *A61K 47/48* | (2006.01) |
| *C07K 16/28* | (2006.01) |
| *G01N 33/50* | (2006.01) |
| *G01N 33/574* | (2006.01) |
| *A61K 31/70* | (2006.01) |
| *A61K 38/02* | (2006.01) |
| *A61K 38/00* | (2006.01) |

(52) U.S. Cl.
CPC ............ *A61K 39/3955* (2013.01); *A61K 31/70* (2013.01); *A61K 38/02* (2013.01); *A61K 47/48407* (2013.01); *A61K 47/48561* (2013.01); *C07K 16/2803* (2013.01); *G01N 33/5011* (2013.01); *G01N 33/57488* (2013.01); *A61K 38/00* (2013.01); *C07K 2317/77* (2013.01)

(58) Field of Classification Search
None
See application file for complete search history.

(56) References Cited

PUBLICATIONS van der Velden et al. (Blood, 97: 3197-3204, 2001).*
Jordan, C.T., Upchurch, D., Szilvassy, S.J., Guzman, M.L., Howard, D.S., Pettigrew, A.L., Meyerrose, T., Rossi, R., Grim, "The Interleukin-3 Receptor Alpha Chain is a Unique Marker for Human Acute Myelogenous Leukemia Stem Cells", "Leukemia", Oct. 1, 2000, pp. 1777-1784, vol. 14, No. 10, Publisher: Macmillan Publishers Ltd, Published in: London, UK
Nguyen, D.H., Ball, E.D., and Varki, A., "Myeloid precursors and acute myeloid leukemia cells express multiple CD33-related Siglecs", "Experimental Hematology ", Jun. 1, 2006, pp. 728-735, vol. 34, No. 6, Publisher: Elsevier Inc., Published in: New York, NY, US
Sievers, E.L., Appelbaum, F.R., Spielberger, R.T., Forman, S.J., Flowers, D., Smith, F.O., Shannon-Dorcy, K., Berger, M., "Selective Ablation of Acute Myeloid Leukemia Using Antibody-targeted Chemotherapy: A Phase I Study of an Anti-CD33 Calic", "Blood", Jun. 1, 1999, pp. 3678-3684, vol. 93, No. 11, Publisher: W.B. Saunders Company, Published in: Orlando, FL, US.
Varki, A. and Angata, T., "Siglecs—the Major Subfamily of I-type Lectins", "Glycobiology", Jul. 13, 2005, pp. 127, vol. 16, No. 1, Publisher: Oxford University Press, Published in: Oxford, UK.
Virgo, P., Denning-Kendall, P.A., Erickson-Miller, C.L., Singha, S., Evely, R., Hows, J. M. and Freeman, S.D., "Identification of the CD33-related Siglec Receptor, Siglec-5 (CD170), as a useful Marker in Both Normal Myelopoiesis an", "British Journal of Haematology", Nov. 1, 2003, pp. 420-430, vol. 123, No. 3, Publisher: Blackwell Publishing, Published in: Edinburgh, UK.
Zhang, J.Q., Nicoll, G., Jones, C. and Crocker, P.R., "Siglec-9, a Novel Sialic Acid Binding Member of the Immunoglobulin Superfamily Expressed Broadly on Human Blood Leukocyt", "Journal of Biological Chemistry", Jul. 21, 2000, pp. 22121-22126, vol. 275, No. 29, Publisher: American Society for Biochemistry and Molecular Biology, Inc., Published in: Bethesda, MD, US.

* cited by examiner

*Primary Examiner* — Misook Yu
*Assistant Examiner* — Nelson B Moseley, II
(74) *Attorney, Agent, or Firm* — Beusse Wolter Sanks & Maire, PLLC; Eugene Molinelli

(57) ABSTRACT

The present invention relates to agents capable of binding sialic acid-binding immunoglobulin-like lectin-9 (Siglec-9) and their use in the treatment of cell proliferation and differentiation disorders. Furthermore, the present invention provides associated pharmaceutical formulations and methods.

13 Claims, 8 Drawing Sheets

SIGLEC-9 BINDING AGENTS

CROSS-REFERENCE TO RELATED APPLICATIONS

Figure 1:
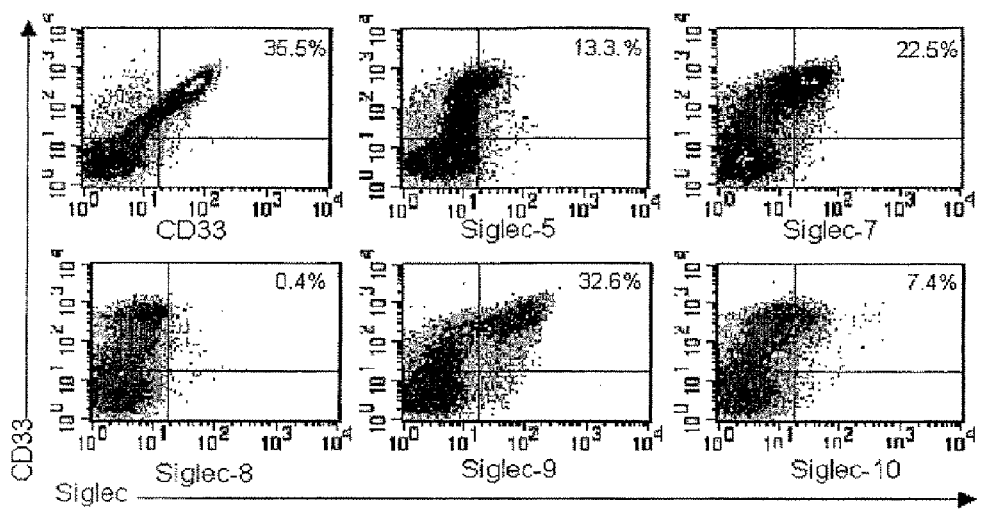

This application claims benefit as a Continuation Application of application Ser. No. 12/884,120 which claims benefit of Divisional Continuation of application Ser. No. 12/091,749, filed Aug. 1, 2008, which claims benefit of PCT Application No. PCT/GB2006/003983, filed Oct. 27, 2006, and United Kingdom Application No. GB0521991.0, filed on Oct. 28, 2005, the entire contents of which are hereby incorporated by reference as if fully set forth herein, under 35 U.S.C. §120.

FIELD OF THE INVENTION

The present invention relates to agents which bind the cell surface marker Siglec-9 and their use in the treatment of cell proliferation disorders and assays.

BACKGROUND

Sialic acid-binding immunoglobulin-like lectins (Siglec(s)) are I-type lectins that are expressed by a number of cells including cells of the haematopoietic system. The Siglecs comprise a number of families of molecules, each characterised by the presence of a N-terminal V-set Ig-like domain, which mediates sialic acid binding, followed by varying numbers of C2-set Ig-like domains[4].

CD33 and the CD33 related siglecs encompass eight of the 11 human siglecs. These molecules share a high degree of sequence similarity and show significant differences in composition amongst mammalian species. The genes encoding these receptors are clustered on chromosome 19q13.3-13.4 and appear to be predominantly expressed in the haematopoietic and immune systems and exhibit differential expression patterns on most mature cells of the innate immune system including monocytes, macrophages, natural killer cells, neutrophils, eosinophils, basophils, mast cells and dendritic cells[6-14]. All human CD33-related siglecs possess a conserved membrane proximal immunoreceptor tyrosine-based inhibition motif (ITIM), as well as a membrane distal ITIM-like motif in their cytoplasmic tails[5].

Acute myeloid leukaemia (AML) describes a group of related haematological malignancies resulting from the abnormal proliferation and differentiation of haematopoietic stem cells (HSC) or progenitor cells[1]. In AML, cells fail to differentiate to normal mature blood cells and instead, proliferate uncontrollably. The resulting immature myeloid cells or blast cells, accumulate and rapidly replace bone marrow leading to a decrease in production of red blood cells, white blood cells and platelets. The loss of red blood cells may lead to complications such as anaemia, infection and bleeding. In some cases the blast cells occasionally invade the lymphatic system, spleen or other vital organs.

AML is classified using a combination of morphological and genetic features, with classification evolving from the French-American-British (FAB)[2] to the World Health Organisation[3] systems. This classification system describes the differentiation status of the predominant leukaemic (blast) cells. The degree of differentiation increases with the subtypes M0, M1, M2 and M3, while subtypes M4 and M5 are mostly monocytic in lineage and types M6 and M7 have features of erythrocytes and megakaryocytes respectively[27].

Leukaemia may be described as abnormal haematopoietic tissue that is initiated by a leukaemic stem cell (LSC) that undergoes an aberrant and poorly regulated process of organogenesis, analogous to that of the normal haematopoietic stem cells (HSC). At present normal haematopoietic stem cells are regarded as $CD34^+$, $CD33^-$, $CD38^-$, $CD71^-$, $CD117^{+/-}$, $CD123^-$, $Lin^-$ while the LSC are regarded as $CD34^+$, $CD33^{+/-}$ $CD38^-$, $CD71^-$, $CD117^{+/-}$, $CD123^+$, $Lin^-$. Mutations in the HSC or early progenitors lead to the development of the LSC, which has self renewal capacity. The LSC gives rise to progenitor cells which proliferate and differentiate to leukaemic blast cells.

The exclusive presence of CD33 on AML cells provides a useful marker for the detection of AML cells and a target for antibody based therapies. Mylotarg® is a humanized anti CD33 monoclonal antibody coupled to the potent antibiotic Calicheamicin-$\gamma_1$ which has been approved for the treatment of relapsed AML following chemotherapy.

The present invention is based upon the observation by the inventors that the CD-33 related Siglec, Siglec-9 is absent from normal bone marrow myeloid progenitor but expressed in AML and as such provides a potential new target for therapies against cell proliferation and/or differentiation disorders. In particular it is noted that Siglec-9 is expressed on subsets of AML cells associated with severe disease (M4 and M5 FAB classification). Furthermore it has been found that unlike CD33 and Siglec-5, the levels of Siglec-9 in the bone marrow plasma were low or undetectable.

It is among the objects of the present invention to provide additional means of treating cell proliferation and or differentiation disorders, for example, acute myeloid leukaemia, and which mitigate or obviate the problems associated with the prior art.

SUMMARY OF THE INVENTION

In a first aspect, the present invention provides a use of sialic acid-binding immunoglobulin-like lectin-9 (Siglec-9) binding agents for the manufacture of a medicament for the treatment of cell proliferation and/or differentiation disorders.

It is to be understood that the term "cell" may refer to any cell or cell type which expresses Siglec-9 or is Siglec-9$^+$. In particular, the term "cell" may refer to cells of the immune system, for example the peripheral blood leukocytes such as, for example, $CD8^+$ T cells, B cells, natural killer (NK) cells ($CD16^{++}/CD56^-$ & $CD16^+/CD56^+$), monocytes, macrophages and neutrophils. In addition, the term "cell" also encompasses cells of the bone marrow, for example, the haematopoietic stem cells.

In addition, the term "proliferation and/or differentiation disorders" encompasses disorders such as cancer. In particular, "proliferation and/or differentiation disorders" may relate to haematological malignancies including, for example, malignant disorders of the monocytic, macrophage and histiocytic lineage and may also include acute myeloid lukeaemia (AML). Table 1 details a number of diseases which are to be considered encompassed by the terms "proliferation and/or differentiation" disorders in accordance with the present invention.

TABLE 1

Cell proliferation disorders and the corresponding WHO classification assignment code.

| Disease | WHO classification |
|---|---|
| AML with inv(16)(p13q22) | WHO 9871/3 |
| Acute myelomonocytic leukaemia | WHO 9867/3 |
| Acute monoblastic and monocytic leukaemia | WHO 9891/3 |
| Chronic myelomonocytic leukaemia | WHO 9945/3 |

TABLE 1-continued

Cell proliferation disorders and the corresponding
WHO classification assignment code.

| Disease | WHO classification |
| --- | --- |
| Juvenile myelomonocytic leukaemia | WHO 9946/3 |
| Histiocytic sarcoma | WHO 9755/3 |
| Langerhans cell histiocytosis | WHO 9751/1 |
| Langerhans cell sarcoma | WHO 9756/3 |

Binding agents of the present invention may bind to or otherwise associate with Siglec-9, and may include, for example, small organic molecules, peptides, carbohydrates or antibodies.

Advantageously the binding agent may be an antibody, for example a polyclonal antibody or a monoclonal antibody which specifically binds to Siglec-9. Advantageously, the antibody does not induce complement mediated or antibody dependant cellular cytotoxicity (ADCC). The techniques used to generate monoclonal antibodies are well known in the art and an exemplary monoclonal antibody is described by Zhang et al, 1996 (J. Biol. Chem. 225: 22121-22126). Furthermore, a person of skill in the art would be able to further modify antibodies (or other binding agents) of the present invention by, for example, modification of the nucleic acid encoding such molecules to, for example, and in the case of an antibody remove the heavy and light chains and "humanise" the molecule.

It should be understood that the term "binding agents" is intended to include fragments thereof which retain the ability to bind or otherwise associate with Siglec-9. Advantageously therefore, the term "antibody" may include whole antibody molecules or fragments thereof which specifically bind to or otherwise associate with Siglec-9. Antibodies may readily be fragmented, for example $F(ab)_2$ fragments can be generated by treating an antibody with pepsin. The $F(ab)_2$ fragments may be treated to reduce disulfide bridges to produce Fab fragments. Other techniques allow antibodies to be further fragmented such that they may comprise solely the complimentary determining region(s) (CDR) of the molecule. Such antibody fragments may be known in the art as "domain antibodies" or "nanobodies".

Antibodies of the present invention may be derived from any species especially mammals, for example a horse, a human or a rodent, for example a rabbit, rat or mouse. Advantageously the antibodies may be modified so as to be "humanised". The techniques used to humanise antibodies derived from species other than a human are well known in the art. In addition, the nucleic acid encoding a specific antibody may be isolated and further manipulated so as to, for example, improve the binding specificity, "humanise" or adjust the size and/or structure of the molecule. It may be possible, to isolate the nucleic acid encoding the Siglec-9 binding agent, for example an anti-Siglec-9 antibody, by removing specific regions of the nucleic acid encoding the binding agent, to reduce the molecule to comprising specific domains such as, for example, the variable region of an antibody. In addition, it may be possible to alter certain residues comprising the molecule to modulate the structure and/or binding specificity.

Alternatively, the Siglec-9 binding agent may comprise the natural ligand for Siglec-9, or, a fragment, analogue or portion thereof. For example the Siglec-9 binding agent may comprise a carbohydrate which further comprises sialic acid. In addition however other peptide or carbohydrate ligands may easily be identified by screening, for example, peptide phage display libraries, glycopeptide libraries or FV phage display libraries.

The Siglec-9 binding agent may modulate the activity of Siglec-9 and/or may modulate the proliferative and/or differentiative state of a cell, including abnormally or aberrantly proliferating and/or differentiating cells. It should be understood that an "abnormally or aberrantly proliferating and/or differentiating cell" is a cell that, when compared to a normally proliferating or appropriately differentiating cell, exhibits up or down regulated levels of proliferation and/or inappropriate differentiation.

The level of proliferation exhibited by a cell may be tested by means well known in the art. For example, the level of incorporation of radioactive nucleotide analogues such as [3H] thymidine, into newly synthesised nucleic acid, may be used as an indication of a cell's proliferative state. Alternatively, non-radioactive nucleotide analogues, such as, for example Bromodeoxyuridine (BrdU), may also be used to indicate the proliferative status of a cell. The amount of radioactive analogue incorporated into newly synthesised DNA may be determined by means of scintillation counting or autoradiography. Alternatively, and where non-radioactive nucleotide analogues are used (e.g. BrdU), the level of analogue incorporation into newly synthesised nucleic acid may be determined by the use of antibodies, or other molecules, which specifically bind to the nucleotide analogue. It may also be possible to determine the proliferative state of a cell by examining the ability of a cell to maintain and propagate itself in culture, or to detect the presence of certain antigens or markers which are indicative of a proliferating cell. Similarly the differentiative state of a cell may be determined by the presence of specific cell markers or by morphological analysis. In addition, it may be possible to monitor the proliferation of a particular population of cells by the addition of a fluorescent dye such as, for example, carboxyfluorecein diacetate succinimidyl ester (CDSE) and the use of flow cytometry. In such cases, as the cells proliferate the level of dye per cell decreases with each division.

Preferably, the Siglec-9 binding agent, once bound, is internalised such that the binding agent is delivered to the interior of the cell or to a compartment or vesicle within the cell. In one embodiment of the present invention the Siglec-9 binding agent may initiate and/or affect its internalisation. Alternatively however, the binding agent may bind or otherwise associate with Siglec-9 but may not be internalised. As such the Siglec-9 binding agent may modulate the proliferative and/or differentiative state of a cell while bound at the cell surface or upon internalisation.

Advantageously the Siglec-9 binding agent may comprise a binding portion, capable of interacting/binding or otherwise associating with Siglec-9, and an active portion capable of modulating the proliferative and/or differentiative state of a cell. The active portion of the binding agent may, for example, be fused, linked, bound, conjugated, joined or otherwise associated with the binding portion and hereinafter, the active portion of the binding agent is to be regarded as "linked" to the binding portion.

Additionally, or alternatively, the active portion of the binding agent may comprise a heterologous molecule, for example a small organic molecule, peptide, carbodhydrate or nucleic acid, linked to the binding portion of the Siglec-9 binding agent.

The techniques used to fuse, link, bind, conjugate, join or associate one molecule to another are well known in the art and are described by Harlow & Lane in "Antibodies: A Laboratory Manual" and by B. Lo in "Antibody Engineering:

Methods and Protocols". A molecule, for example a peptide, may be fused, linked, bound, conjugated, joined or otherwise associated with an antibody by means of the recombinant techniques discussed in detail in "Molecular Cloning: A Laboratory Manual" by Sambrook and Russell. Alternatively, covalent interactions between molecules may be established under certain conditions and after suitable preparation of the molecules to be linked.

Advantageously, the binding portion and the active portion of the Siglec-9 binding agent may be linked together such that upon exposure to certain conditions or agents, the linked molecules are separated. In the present case, the binding portion and active portion of the Siglec-9 binding agent may be linked together by a linking region which may comprise a portion which is sensitive to enzymatic cleavage or changes in environmental conditions such as salt concentration, pH and/or temperature. Such linking regions are well known in the art and may include, for example, moieties capable of affecting the hydrolytic release of, for example, the active portion from the binding portion of the Siglec-9 binding agent in response to, for example, a change in pH.

Thus, where the Siglec-9 binding agent is capable of modulating the proliferative and/or differentiative state of a cell, the term "active portion" may be taken to refer to the Siglec-9 binding agent as a whole. Alternatively however, the temrm "active portion" may be taken to refer to a portion of the binding agent. Moreover "active portion" may also refer to a molecule, heterologous or otherwise, which, through any means described herein and known in the art, is linked to the Siglec-9 binding agent.

Advantageously, and once bound to Siglec-9, the active portion of the Siglec-9 binging agent may be internalised such that its activity is directed to the interior of the cell. Alternatively, the active portion of the Siglec-9 binding agent may remain at or near the cell surface from where it may modulate the proliferative and/or differentiative state of a cell.

The active portion may, for example, render an abnormally or aberrantly proliferating and/or differentiating cell, quiescent or dead. In one embodiment of the present invention the active portion may, for example, modulate some aspect of cell metabolism or cause a cell to die. Cell death may occur as a result of exposure to a toxic substance, for example a heavy metal, toxin or toxoid, or via the activation of programmed cell death pathways (apoptosis). In addition, cell death may occur, for example, via the induction of cell lysis, the modulation of one or more aspects of cell metabolism and/or modulation of cell systems such as cell membrane pumps/transporters or protein synthesis components.

The active portion of the Siglec-9 binding agent may comprise a cytotoxic moiety which may result in cell death or may render certain pathways, proteins, molecules or nucleic acids inactive, inhibited or otherwise modulated such that the cell is unable to function correctly. Additionally, the Siglec-9 binding agent may increase or decrease the rate of certain metabolic pathways, or may modulate the production of certain proteins, nucleic acids or other molecules such that the cell is unable to function correctly.

Siglec-9 binding agents of the present invention may also may also include agents which specifically modulate protein and/or nucleic acid synthesis. For example the binding agent may modulate or interact with specific enzymes or ribosomes.

It is particularly advantageous to use Siglec-9 as a target molecule for binding agents of the present invention, as the levels of cell-free Siglec-9 are considerably lower than for other related Siglecs. It should be noted that "cell-free Siglec" refers to Siglec molecules which are not associated with a cell and which are detectable in the plasma fraction of whole blood. Accordingly "cell-free" Siglec-9 may also be referred to as or "soluble" or "plasma" Siglec-9. By way of example, the level of Siglec-5 and CD-33 detectable in plasma is significantly higher than the level of Siglec-9 and as such, binding agents with specificity for Siglec-9 are less likely to be neutralised or absorbed by soluble ligand. Thus, Siglec-9 binding agents may be more efficacious than binding agents specific for other siglec molecules.

It has been observed that Siglec-9 is expressed on subsets of AML cells associated with severe disease. As such, the use of Siglec-9 as a target molecule for agents of the present invention may facilitate the identification and/or diagnosis of patients with severe disease (M4 and M5 FAB classification) and/or may provide an effective drug target for severe disease.

In one embodiment of the present invention, the active portion of the Siglec-9 binding agent may comprise the cytotoxic agent calicheamicin-yl.

Thus in a second aspect of the present invention there is provided a use of a siglec-9 binding agent for the treatment of cell proliferation and differentiation disorders, wherein the Siglec-9 binding agent comprises an antibody which specifically binds to Siglec-9 conjugated to calicheamicin-γ1.

Advantageously, the Siglec-9 binding agents described herein may be formulated as sterile pharmaceutical compositions comprising a pharmaceutically acceptable carrier, diluent or excipient. Such carriers, diluents or excipients are well known to one of skill in the art and may include, for example, water, saline, phosphate buffered saline, dextrose, glycerol, ethanol, ion exchangers, alumina, aluminium stearate, lecithin, serum proteins, such as serum albumin, buffer substances such as phosphates, glycine, sorbic acid, potassium sorbate, partial glyceride mixtures of saturated vegetable fatty acids, lactic acid, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cyclodextrins, such as αcyclodextrin, βcyclodextrin, sulfobutylether$_7$-βcyclodextrin and hydroxypropyl-β-cyelodextrin, cellulose-based substances, polyethylene glycon, sodium carboxymethylcellulose, polyacrylates, waxes, polyethylene-polypropylene-block polymers, polyethylene glycol and wool fat and the like, or combinations thereof.

Further more, the Siglec-9 binding agents may be administered in combination with another treatment. For example, Siglec-9 binding agents may be administered in combination with agents capable of binding other Siglecs, for example Siglec-3 or 5. Additionally or alternatively, the Siglec-9 binding agent may be administered in combination with antibiotic, antifungal or antiviral agents or in combination with a chemotherapeutic agent, an immunostimulatory compound or drug, an oligonucleotide, a cytokine, hormone or the like.

In a second aspect of the present invention there is provided a method of treating a subject having a cell proliferation and/or differentiation disorder comprising administering to said subject an effective amount of an agent capable of binding Siglec-9.

The medicaments described herein may be formulated to comprise one or more binding agents. For example, the medicament may comprise one or more Siglec-9 binding agents or a Siglec-9 binding agent and an agent capable of binding another component of a Siglec-9$^+$ cell. For example, the medicament may further comprise agents which are capable of binding CD33 or a CD33 related. Siglec.

In a third aspect of the present invention, there is provided a method of screening for agents capable of binding Siglec-9 said method comprising the steps of;
 a) contacting a test agent with a cell expressing Siglec-9; and
 b) detecting an interaction between the test agent and Siglec-9.

Interactions between molecules may be detected by techniques such as polyacrylamide gel-electrophoresis (PAGE), enzyme linked immunosorbant assay (ELISA), Western blot or immunoblot. By way of example, cells expressing Siglec-9 or the Siglec-9 molecule may be adhered or coated on to, for example, the surface of a microtitre plate. A test agent may then be applied to the cells or Siglec-9, under conditions permitting the interaction of Siglec-9 with the test agent. After a suitable wash step an antibody either specifically reactive to Siglec-9 or to the test agent may be added under conditions suitable to permit the interaction of said antibody with its epitope. Antibody-antigen interactions may then be detected by any suitable means. For example the antibody may be conjugated to a compound capable of reporting a level of bound antibody by a colorimetric, chemiluminescent or bioluminescent reaction. such compounds may include, but are not limited to, horse radish peroxidase (HRP) and alkaline phosphatase (AlkP). Additionally or alternatively, binding between a test agent and Siglec-9 may be determined by means electrophoresis techniques such as, for example, a "band shift" assay. By way of example, a test agent may first be incubated or contacted with Siglec-9, under conditions permitting the interaction of Siglec-9 with the test agent. Such an incubation period may result in the formation of a Siglec-9/test agent complex and such complexes may easily be detected by subjecting a sample to electrophoresis. Specifically, the presence of a Siglec-9/test agent complex may be detected by comparing the migration of the sample with the migration of a control sample under electrophoresis. It is to be expected that a Siglec-9/test agent complex would migrate less than either Siglec-9 or the test agent when subjected to electrophoresis independently. Altered migration under electrophoresis may manifest as a "band shift". By "control sample", it is meant a sample of Siglec-9 or test agent which has not been contacted to either Siglec-9 or test agent prior to electrophoresis.

The above described method may be altered so as to provide a method of screening for agents which bind to Siglec-9 and which are also capable of modulating the proliferative and/or differentiative state of a cell. Such a method may comprise the steps of
 a) contacting a test agent with a cell expressing Siglec-9; and
 b) comparing the proliferation and/or differentiation of the cell of step (a) with a control cell.

It is to be understood that the cell used in step (a) may be an abnormally or aberrantly proliferating cell. Alternatively, the cell may be a normally proliferating or normally or appropriately differentiated cell.

It is to be understood that "control cell" relates to a cell which corresponds to that used in the test agent screening assay (step a), but which has not been exposed or contacted to the test agent.

Alternatively the method may comprise the additional step of fusing, linking, binding, conjugating, joining or associating a test agent to/with a known Siglec-9 binding agent to form a "hybrid" Siglec-9 molecule and contacting a cell with the "hybrid" Siglec-9 binding agent. In this way it may be possible to determine whether or not an agent is capable of modulating the proliferative and/or differentiative state of cell by comparing the proliferation and/or differentiation of the cell with a control cell as described above. In this particular method, in addition to the use of a control cell which has not been exposed to the test agent, it may be desirable to use a control cell which has not been exposed to the known Siglec-9 binding agent. In this way it would be possible to determine whether any observed effect upon cell proliferation or differentiation was due to the test agent.

It may be possible to determine the proliferative state of a cell by using the techniques described in detail above. Briefly, these may include the use of radioactive and non-radioactive nucleotide analogues and/or the detection of certain antigens or markers which are indicative of a particular state of proliferation. Similarly, the differentiative state of a cell may be determined by the presence of specific cell markers or by morphological analysis.

In a fourth aspect of the present invention, there is provided a method of detecting a cell proliferation and/or differentiation disorder in a sample obtained from a subject suspected of having a cell proliferation and/or differentiation disorder, said method comprising the steps of subject comprising the steps of;
 a) obtaining a sample from a patient;
 b) contacting the sample with an agent capable of binding Siglec-9; and
 c) detecting an interaction between the binding agent and Siglec-9,
wherein the presence of Siglec-9 is indicative of a cell proliferation and or differentiation disorder.

The method may further comprise the step of comparing the level of Siglec-9 detected in the sample derived from the subject, with the level of siglec-9 present in a control sample. By "control sample" it is meant a sample, preferably obtained from a substantially identical tissue or body fluid, but which is derived from a subject or source not having a cell proliferation and or differentiation disorder.

A suitable sample may include a sample or biopsy of a particular tissue or body fluid. For example a cell proliferation and/or differentiation disorder may be detected in samples of tissue comprising cells and obtained from, for example, the bone marrow or lymph nodes, or from body fluid samples such as blood or saliva.

In a fifth aspect of the present invention, there is provided a method of obtaining abnormally or aberrantly proliferating and/or differentiating cells, said method comprising the steps of;
 a) immobilising a siglec-9 binding agent on to a support substrate; and
 b) contacting said immobilised Siglec-9 binding agent with a cell sample.

The solid support may, for example, be agarose, sepharose, polyacrylamide, agarose/polyacrylamide co-polymers, dextran, cellulose, polypropylene, polycarbonate, nitocellulose, glass paper or any other suitable substance capable of providing a suitable solid support.

Advantageously, the solid support may be in the form of granules, a powder or a gel suitable for use in chromatography such as those available from Amersham Biosciences.

The Siglec-9 binding agent may further comprise a binding moiety providing a means of coupling said Siglec-9 binding agent to the solid support. Such a binding moiety could be for example a peptide or other small chemical moiety, for example biotin/streptavidin.

In a further embodiment of the present invention, the binding moiety may comprise any of the oligopeptides $His_n$, where n is 4-20, preferably n is 5-10 and more preferably n is 6. Such oligopeptides have a high affinity for divalent nickel (Ni), enabling the Siglec-9 binding agent to be coupled to the nickel chelating resin $Ni^{2+}$—NTA-agarose.

Alternatively, and in a further embodiment of the present invention, the Siglec-9 binding agent may be chemically cross-linked to the solid support. Advantageously the Siglec-9 binding agent may be chemically cross-linked to the solid support by means of, for example, activation of the solid support by the addition of cyanogen bromide (CNBr) as disclosed by Axen et al (1967). Briefly, upon addition of CNBr the solid support reacts rapidly at pH 8-9 with free amino acid groups in the polypeptide to be cross-linked to the solid support. Preferably the solid support for use in this way is agarose, for example CNBr-activated agarose.

Advantageously, the Siglec-9 binding agent may be coupled to the solid support by means of an antibody or fragment thereof which specifically reacts with a portion of said binding agent. Preferably the antibody is coupled to the suitable solid support. Advantageously, the antibody or fragments thereof useful in this way may be monoclonal antibodies or fragments which have an affinity for the Silec-9 binding agent. The techniques of monoclonal antibody production are well lmown to one of ordinary skill in the art.

Alternatively, the method described above may be used to remove cells expressing siglec-9 from a sample or solution comprising a cell population. In this way it may be possible to remove from a population of cells, those cells which aberrantly proliferate and/or which inappropriately differentiate, so as to obtain a population of cells which consists substantially of cells which normally proliferate and/or differentiate. Cells, for use in this particular method may be derived from blood and/or bone marrow. Accordingly, a sample comprising cells obtained from (or provided by) a patient, or subject with a cell proliferation and/or differentiation disorder such as acute myeloid leukaemia, may be depleted of substantially all of the cells which aberrantly proliferate or inappropriately differentiate. Upon removal of these cells from the cell sample, the remaining cells may be returned to the patient and/or subject.

The method for removing siglec-9 expressing cells from a population of cells may be combined with a process which removes cells which express CD33. For example, a siglec-9 binding agent and a CD33 binding agent may be immobilised on a suitable substrate. By contacting the immobilised siglec-9/CD33 binding agents with a sample comprising a population of cells, those cells expressing CD33 and/or siglec-9 will be removed from the cell population. Additionally, such methods may be combined with chemotherapy to provide a comprehensive treatment strategy to those suffering from a cell proliferation and/or differentiation disorder.

DETAILED DESCRIPTION

The present invention will now be described further by way of example and with reference to the Figures which show:

FIG. 1. Expression of CD33-related Siglecs on AML cells. Mononuclear AML bone marrow cells from sample XXI (see Table 2) were stained with anti-CD33-biotin mAb and the indicated FITC-labelled anti-Siglec mAbs, followed by streptavidin-APC and analysed by flow cytometry. The non-viable cells labelled with 7-AAD were not included in the analyses. The left quadrants were set to include more than 99% of cells labelled by the isotype control. The percentages of $CD33^+/Siglec^+$ cells are shown.

Figure 2:
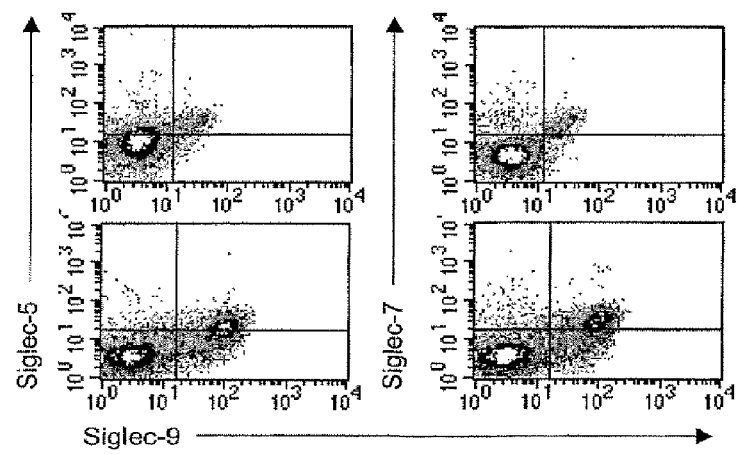

FIG. 2. Co-expression of Siglec-7 and Siglec-5 on the Siglec-9-positive subset of AML cells. Mononuclear AML bone marrow cells from samples I (top panels) and XXI (lower panels) (see Table 2) were stained with anti-Siglec-9-FITC mAb and either anti-Siglec-5-biotin or anti-Siglec-7-biotin mAbs, followed by streptavidin-APC and analysed by flow cytometry.

Figure 3:
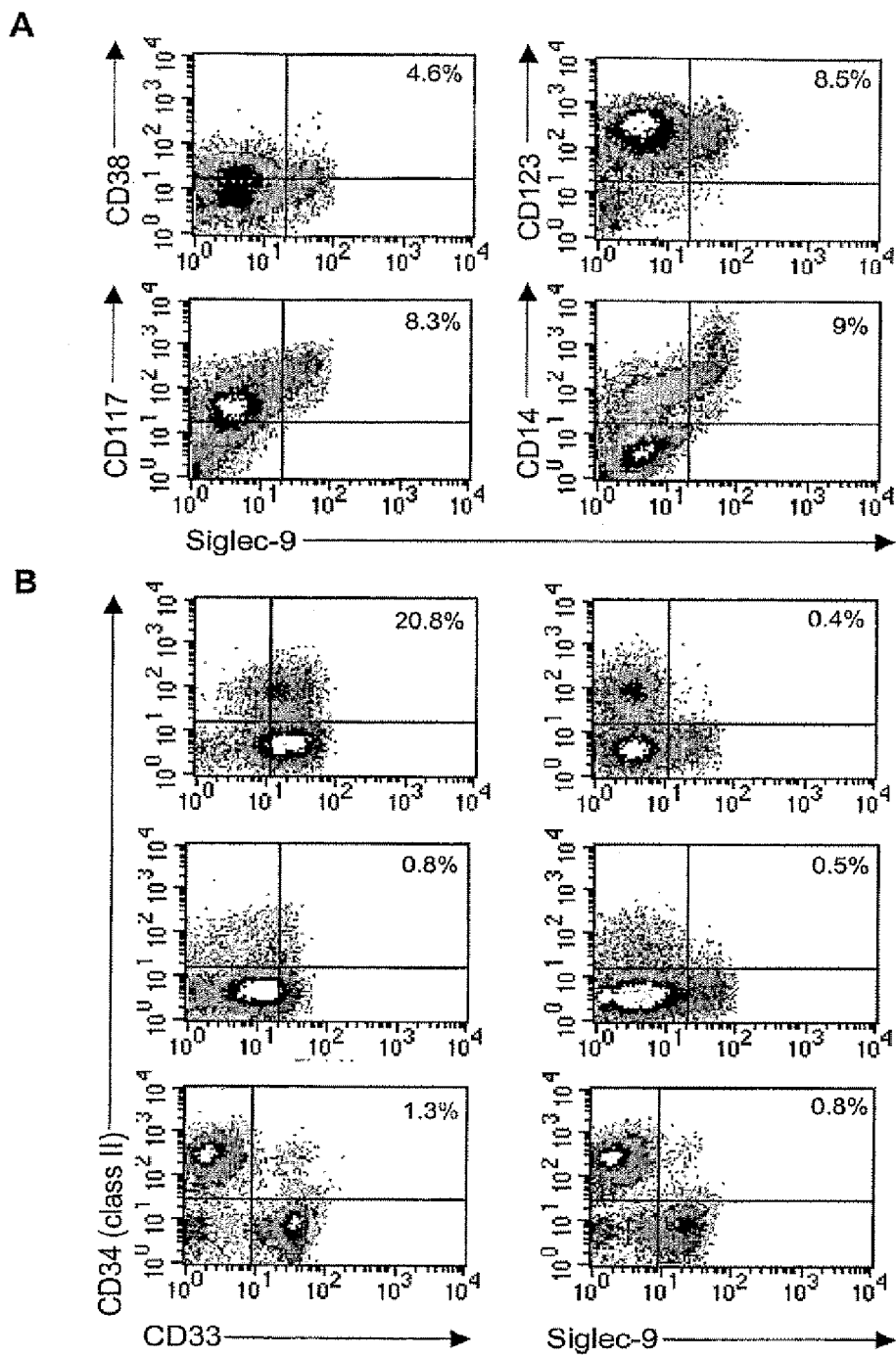

FIG. 3. Phenotypic characterisation of Siglec-9-positive AML cells by flow cytometry. A. Mononuclear AML bone marrow cells from sample II (see Table 2) were stained with anti-Siglec-9-FITC mAb in conjunction with one of the following mAbs: anti-CD38-biotin, anti-CD123-biotin (both followed by streptavidin-APC), anti-CD117-PE or anti-CD14-PE. B. AML cells were stained with anti-CD33-FITC or anti-Siglec-9-FITC mAbs in conjunction with anti-CD34 class II-biotin followed by streptavidin-APC. Examples of 3 AML samples (Table 2) are shown (top panel, sample I, 29% $CD34^+$; middle panel, sample II, 2.5% $CD34^+$; bottom panel sample XIX, 31% $CD34^+$). The percentages of double-positive cells are shown for each dot-plot.

Figure 4:
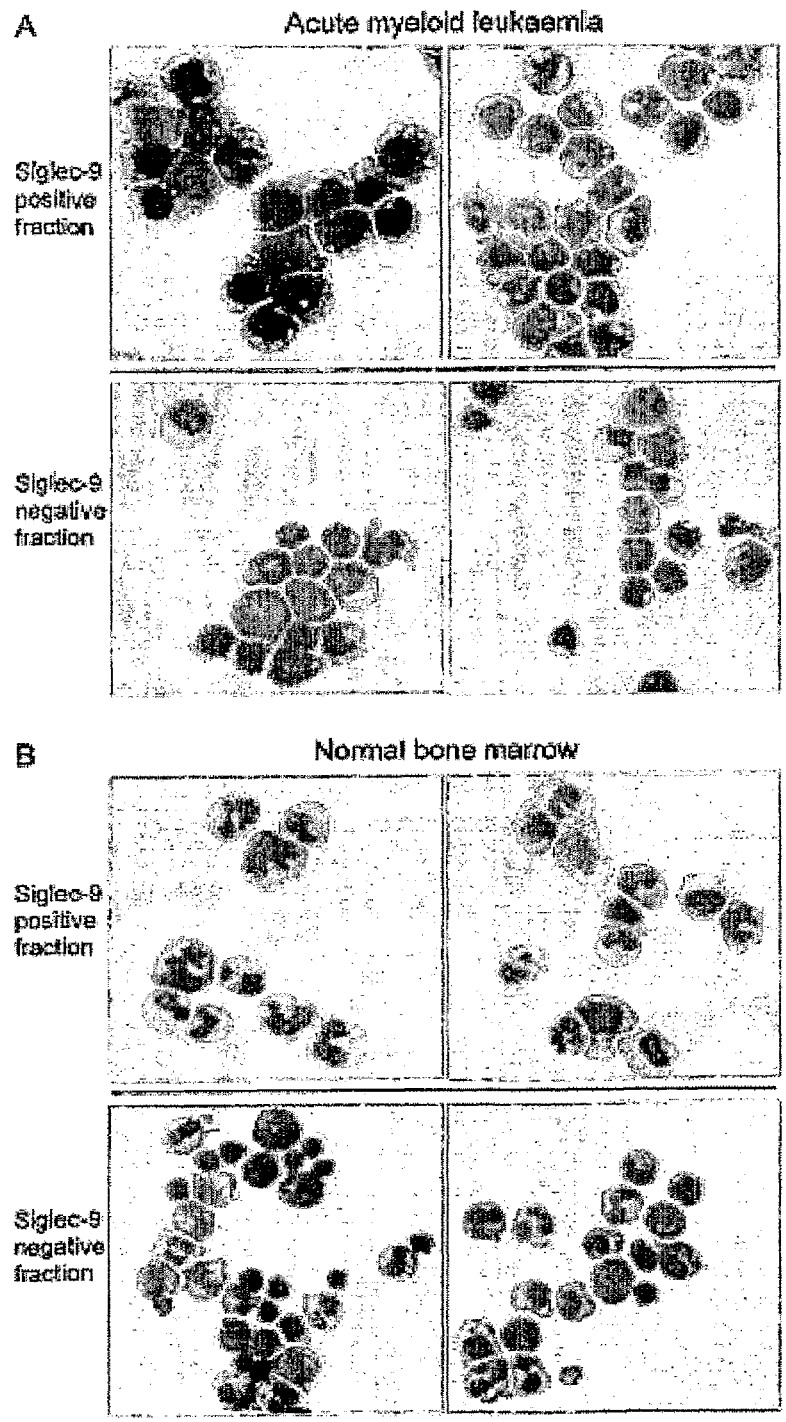

FIG. 4. May-Grunwald-Giemsa staining of AML cells and normal bone marrow cells. Mononuclear AML bone marrow cells (A) and mononuclear not normal bone marrow cells (B) were immunomagnetically sorted into Siglec-9-positive and -negative fractions and cytospins stained using May-Grunwald-Giemsa. Cells within the Siglec-9-positive fractions are enriched for cells of the monocytic lineage.

Figure 5A:
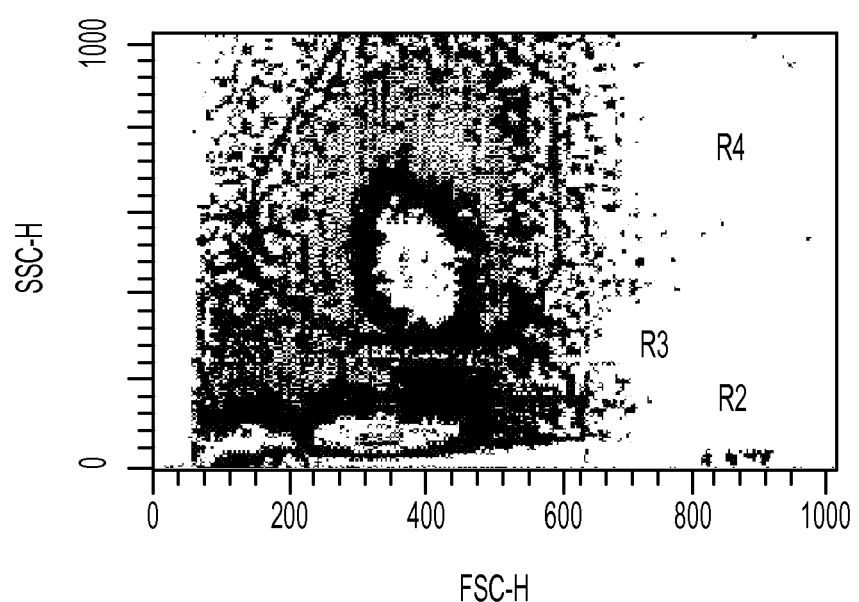
Figure 5B:
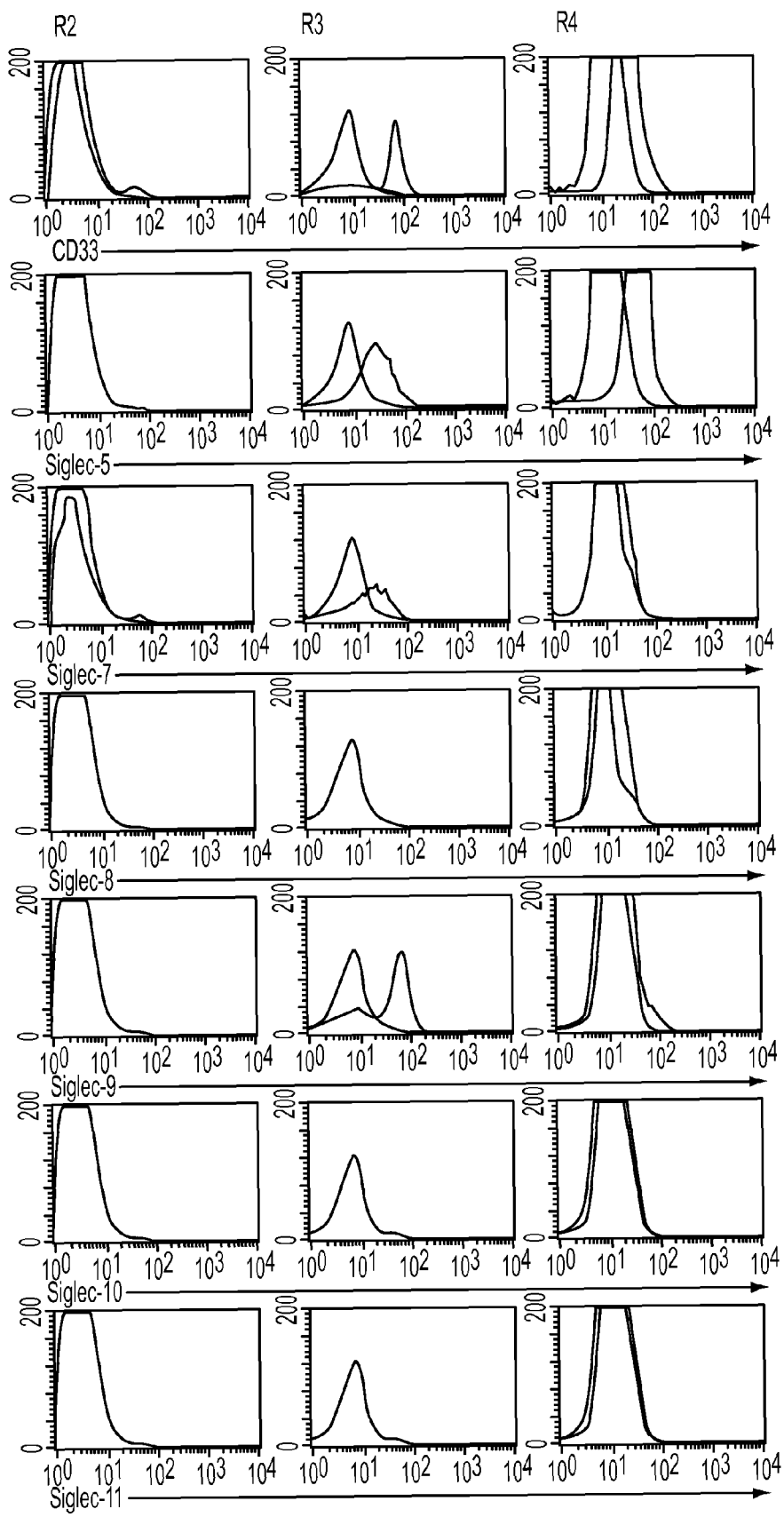

FIG. 5. Expression of CD33-related Siglecs on normal bone marrow cells. Mononuclear bone marrow cells were stained with the indicated FITC-labeled mAbs and analysed by flow cytometry. A. A plot of forward scatter (FSC) versus side scatter (SSC) permits definition of three populations: R2, $SSC^{low}$; R3, $SSC^{medium}$; R4, $SSC^{high}$. B. The grey histograms show expression of CD33-related Siglecs using the indicated mAbs on the three subsets of cells defined above. White histograms show staining with the isotype control.

Figure 6:
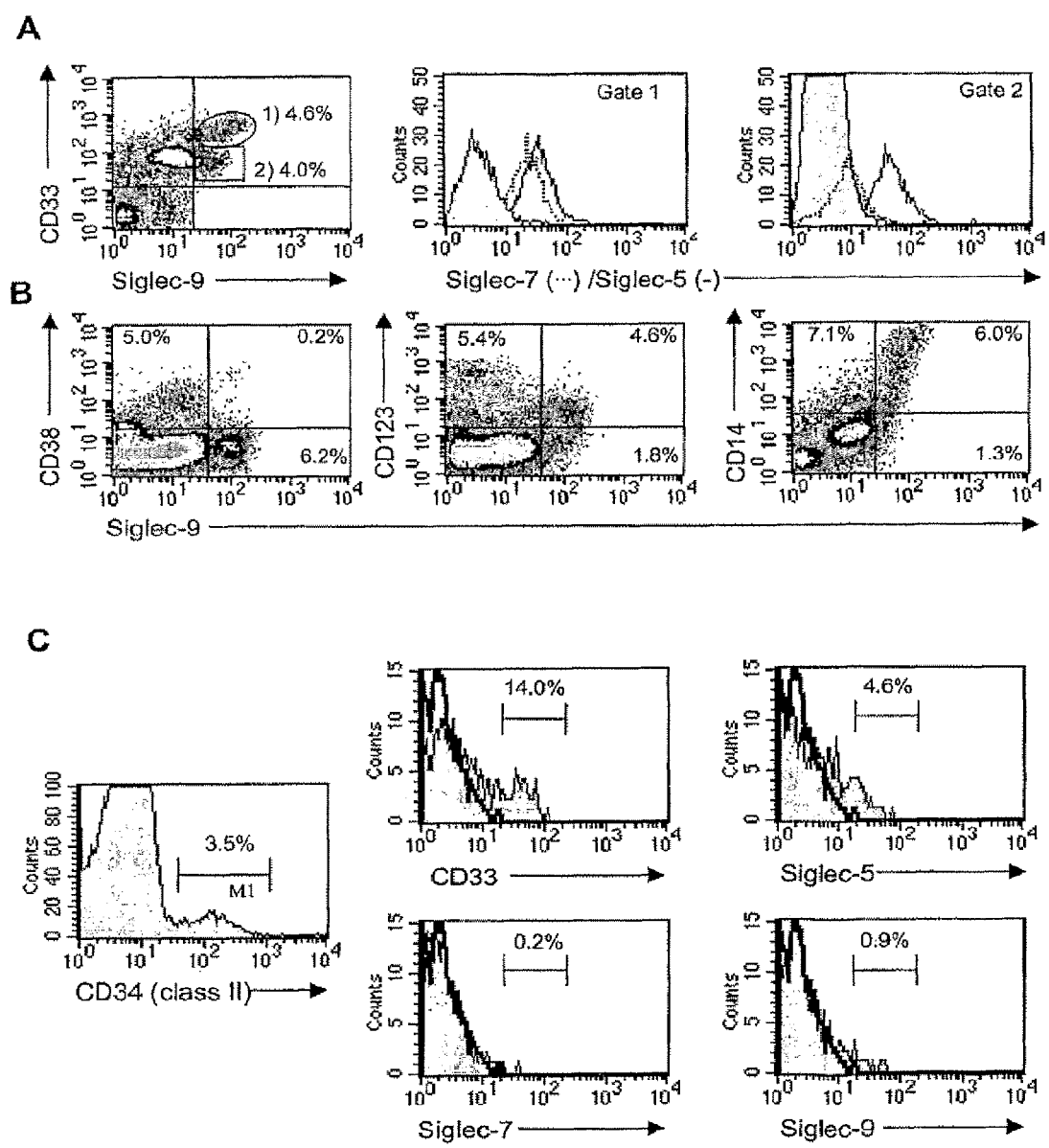

FIG. 6. Characterisation of Siglec-positive subsets in normal bone marrow. A. Bone marrow cells were labeled with anti-CD33-APC and anti-Siglec-9-FITC together with either anti-Siglec-5-biotin or anti-Siglec-7-biotin followed by streptavidin-PE. Two Siglec-9 positive populations are defined: Gate 1, $CD33^{high}$, $Siglec-9^+$; Gate 2, $CD33^{medium}$, $Siglec-9^+$. The histograms show expression of Siglec-5 and Siglec-7 on each gated subpopulation. B. Bone marrow cells were labeled with anti-Siglec-9-FITC together with either anti-CD38-biotin or anti-CD123-biotin followed by streptavidin-APC, or anti-CD14-PE. The percentages of single and double positive cells are shown. C. Bone marrow cells were stained with anti-CD34-biotin and either CD33-FITC, anti-Siglec-5-FITC, anti-Siglec-7-FITC or anti-Siglec-9-FITC followed by streptavidin-APC. The $CD34^+$ cells were gated (M1, grey histogram, left panel) and analysed for expression of CD33, and Siglecs-5, -7 and -9 (grey histograms, right panels). White histograms show labeling of $CD34^+$ cells with isotype matched control.

Figure 7:
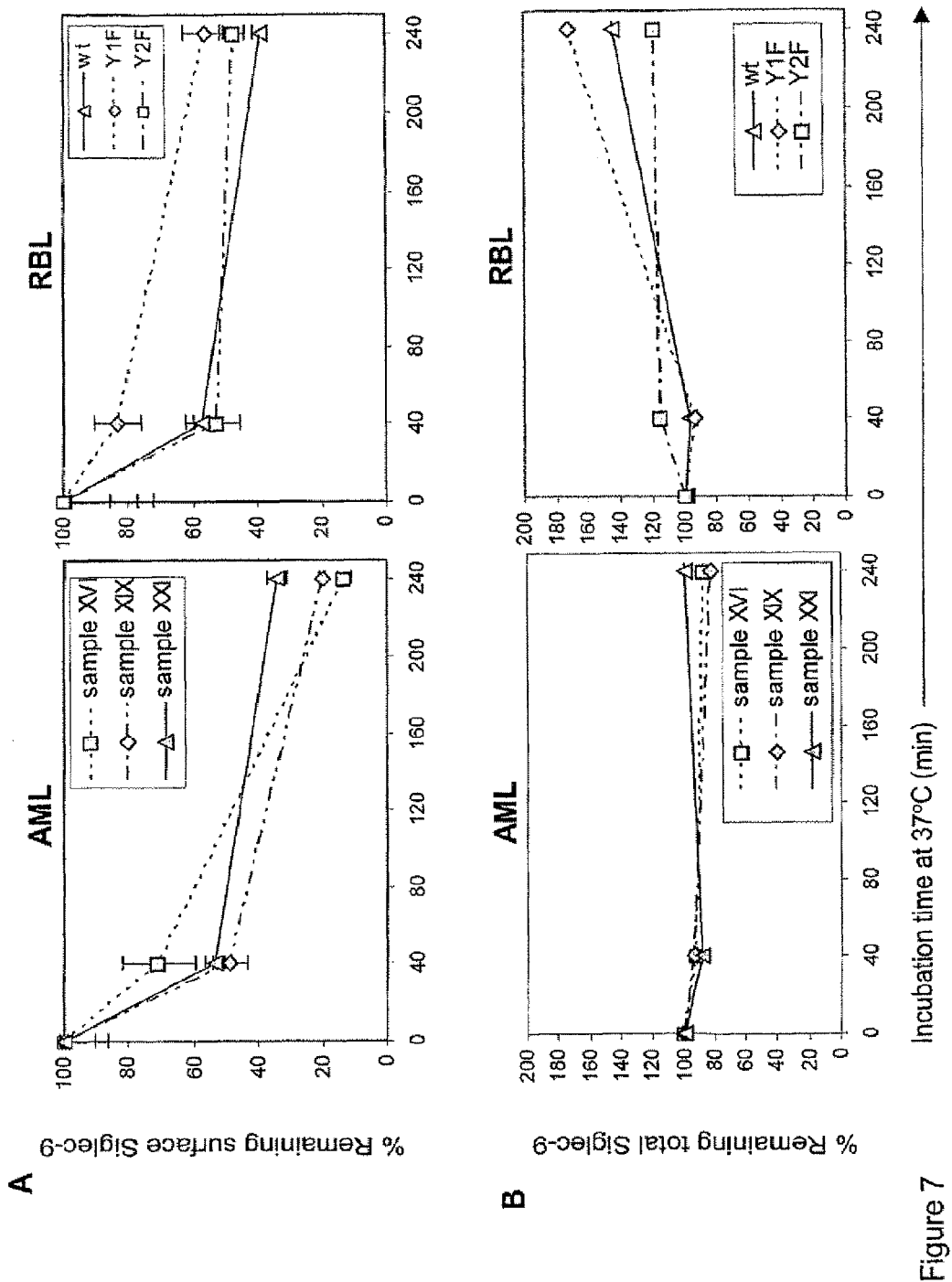

FIG. 7. Internalisation of anti-Siglec-9 mAb. A. Mononuclear AML bone marrow cells from samples XVI, XIX and XXI (left panel) or RBL cells stably transfected with wild type (WT) or (Y1F) or (Y2F) mutant forms of Siglec-9 (right panel) were labelled with anti-Siglec-9-Alexa-488 mAb for 45 min on ice, washed and then incubated for 40 or 240 min at 37° C. The remaining surface anti-Siglec-9 mAb was detected using goat anti-mouse-APC. The graphs show the anti-Siglec-9 mAb remaining at the surface expressed as a percentage of the starting values B. Internalisation assays were carried out as described in (A) and the levels of total cell associated anti-Siglec-9-Alexa-488 was measured at each time point. The increases seen in the right panel reflect a time-dependent gain in autofluorescence of RBL cells detected on the FL-1 channel. The graphs show the total remaining anti-Siglec-9 mAb expressed as a percentage of the starting values.

Figure 8:
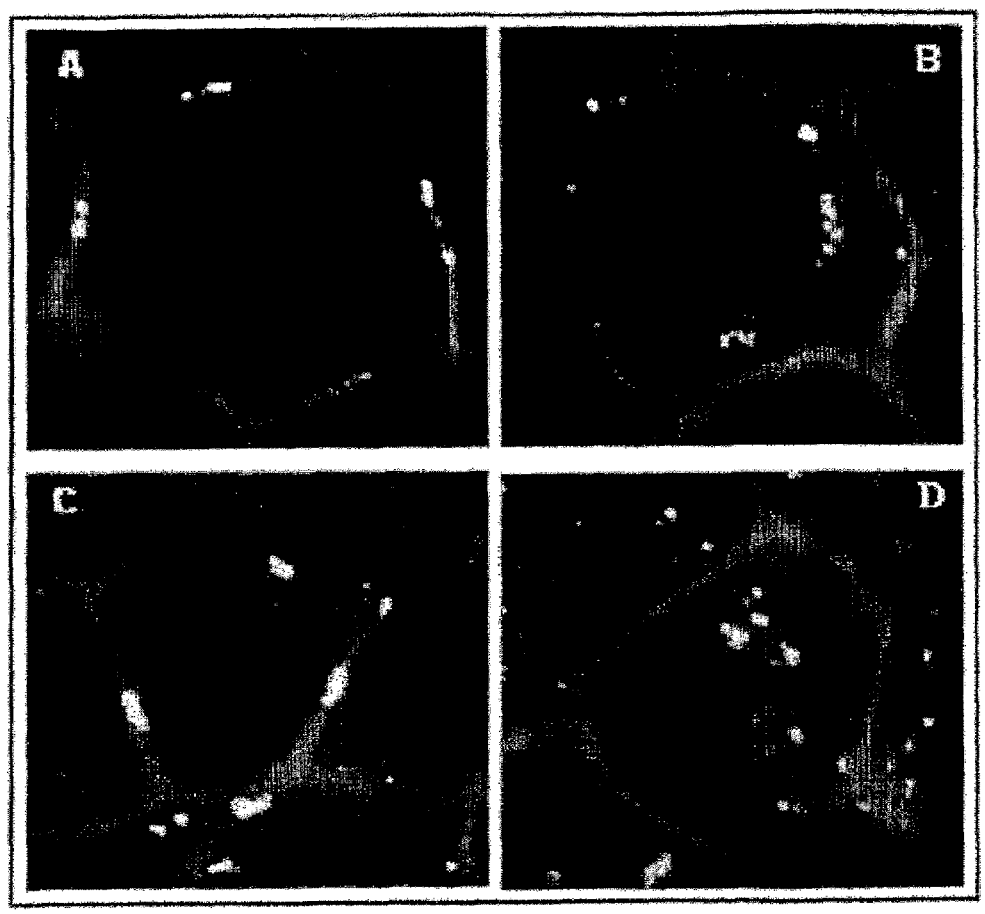

FIG. 8. Confocal microscopy analysis of internalisation of anti-Siglec-9 mAb by transfected RBL cells. WT (A, B) or Y1F (C) or Y2F (D) mutant forms of Siglec-9-transfected RBL cells were incubated on ice with anti-Siglec-9-Alexa-488 mAb for 1 h, washed and incubated for 1 h at 37° C. (B, C, D) or for 1 h on ice (A). Internalization was stopped by chilling on ice and the plasma membrane labeled with cholera toxin B subunit-Alexa-594. After washing, the cells were fixed with 4% paraformaldehyde and examined by confocal microscopy.

MATERIALS AND METHODS

AML Patients and Normal Bone Marrow and Blood Donors

Bone marrow aspirates from AML patients and bone marrow samples from otherwise healthy patients undergoing hip replacement surgery were obtained after informed consent. AML samples were stored in the Tayside Cancer Tissue Bank. The study was approved by the Tayside Cancer Tissue Committee (Ref. 04/S1401/85), which represents the Tayside Committee for Medical Research Ethics for studies involving banked tissue. Mononuclear cells (MNC) were purified by Ficoll-Paque™ Plus (Amersham Biosciences, Bucks, UK) density gradient centrifugation. AML cell aliquots were stored in liquid nitrogen and normal MNC were directly used for the experiments. Cryopreserved samples were thawed and incubated in RPMI 1640 (with L-glutamine) medium supplemented with 20% FCS, 1% penicillin/streptomycin, 10 mM HEPES buffer (all reagents were from Invitrogen Gibco, Paisley, UK) for 90 min at 37° C., 5% $CO_2$ prior to experiments. Bone marrow plasma was prepared by centrifugation of anticoagulated whole bone marrow aspirates and stored at −80° C. Blood samples for preparation of serum were collected from laboratory volunteers according to local ethical guidelines.

Antibodies

Specific monoclonal antibodies (mAbs) to the following CD33-related siglecs were produced in our laboratory: CD33 (6C5), Siglec-5 (1A5)[6], Siglec-7 (S75a)[7], Siglec-8 (7C9)[9], Siglec-9 (KALLI)[11], Siglec-10 (5G6)[12] and Siglec-11 (4C4)[13]. All are mouse IgG1 except 4C4 which is IgG2c. IgGs were purified from tissue culture supernatants using protein G Sepharose (Sigma, Dorset, UK) and labelled with fluorescein-5-isothiocyanate (isomer 1) (FITC) (Invitrogen, Paisley, UK). Anti-Siglec-5 and -Siglec-7 IgGs were labelled with EZ-Link biotin (Pierce, Rockford) and anti-CD33, -Siglec-8 and -Siglec-9 IgGs were labelled with Alexa Fluor 488 (Invitrogen). The following commercial Abs were also used: anti-CD33-biotin (WM53, Serotec, Oxford, UK), anti-CD33-APC (WM53, Serotec), anti-Siglec-6 (E20-1232, BD Pharmingen, Oxford, UK), anti-CD34-biotin (QBEND, Serotec), anti-CD14-PE (Caltag-Medsystems, Buckingham, UK), anti-CD38-biotin (HIT2, Caltag-Medsystems), anti-CD123-biotin (6H6, eBioscience, San Diego, USA), anti-CD 117 (104D2, Caltag-Medsystems), anti-mouse immunoglobulin-FITC (DAKO, Ely, UK).

Flow Cytometry $3-4\times10^5$ cells were stained with saturating concentrations of the indicated mAbs for 45 min on ice. After washing, the cells were incubated with streptavidin-APC or -PE for 30 min on ice and after an additional washing step the cells were resuspended in PBS containing 0.25% bovine serum albumin, 10 mM sodium azide and 7-amino actinomycin D (7-AAD). For Siglec-6 staining, cells were incubated with saturating levels of purified Siglec-6 mAb, followed by anti-mouse IgG-FITC. All flow cytometry analysis was performed using either a FACS Calibur or LSR flow cytometer (BD Biosciences) and CellQuest software. In each case the negative quadrant was set to include more than 99% of the isotype control-labeled cells and the non-viable 7-AAD-positive cells were routinely excluded from all FACS analyses.

May-Grunwald-Giemsa Staining of Siglec-9+ and Siglec-9− Cells

AML cells and normal bone marrow cells were labeled with anti-Siglec-9 IgG-FITC followed by anti-FITC-coupled paramagnetic microbeads and magnetically sorted into positive and negative fractions using an AutoMACS system (Miltenyi Biotech, Bisley UK), according to the manufacturer's instructions. The purity of the separated cell fractions was approximately 90% as assessed by flow cytometry. Cytospins were prepared and stained with May-Grunwald-Giemsa. Images from randomly selected fields were taken with an Axioskop microscope (Zeiss, Jena, Germany), using a 63×1.25 oil lens (Zeiss) and Axiovision 3.0 software. Black and white reference was set according to the manufacturer's instructions and the exposure time was 1273 ms.

Colony Forming Assays

AML cells and normal bone marrow cells were labeled with anti-Siglec-9-FITC and sorted into positive and negative fractions using a FACS Vantage SE (BD Biosciences). The purity of the positive fractions was consistently greater than 95%. To control for the potential effect of anti-Siglec-9 mAb on colony forming ability, all experiments included unsorted cells that had been incubated or not with anti-Siglec-9-FITC. FACS sorted cells and control Ab incubated cells were cultured in methylcellulose media (HSC-CFU complete with erythropoietin, Miltenyi Biotech) for 14 days at 37° C., 5% $CO_2$, and numbers of CFU-E, BFU-E, CFU-G, CFU-M, CFU-GM and CFU-GEMM scored according to the manufacturer's instructions. The CFU-blast assay was carried as described[19], using the same culture conditions as for normal bone marrow cells.

Flow Cytometric Analysis of Anti-Siglec-9 mAb Internalisation

Cells were labeled with anti-Siglec-9-Alexa-488 mAb for 45 min on ice. The cells were washed and either stored on ice or incubated for 60 or 240 min at 37° C., 5% $CO_2$ in complete medium. At each time point, internalization was stopped by placing the tubes on ice. At the end of all incubations, the levels of anti-Siglec-9-Alexa-488 mAb remaining at the cell surface were detected in triplicate using goat anti-mouse-IgG-APC (Caltag-Medsystems) on the FL-4 channel. The total cell-associated Alexa-488-labelled anti-Siglec-9 mAb (surface+internalized) was measured on the FL-1 channel. Anti-Siglec-8-Alexa-488 mAb was used as an isotype control. Internalisation was quantified by subtracting the FL-4 median fluorescence intensity (MFI) obtained with anti-Siglec-8 from the FL-4 MFI obtained with anti-Siglec-9. The FL-4 MFI values of cells kept on ice throughout the experiment were considered as 100%. The total cell-associated anti-Siglec-9 mAb was calculated similarly using the corresponding FL-1 MFI values.

Internalisation Analysed by Confocal Microscopy

Adherent rat basophil leukemia (RBL) cells expressing wild-type or tyrosine to phenylalanine mutant forms of Siglec-9[15] were cultured in 8-well chamber slides (Nalge-Nunc International, VWR, Leics, UK) and incubated with anti-Siglec-9-Alexa-488 mAb for 1 h on ice. After washing, the cells were incubated in complete medium on ice or for the indicated period of time at 37° C., 5% $CO_2$. Internalization was stopped by putting the cells on ice and the plasma membrane labeled with 5 μg/ml cholera toxin B subunit-Alexa-594 (Invitrogen). After washing, the cells were fixed with 4% paraformaldehyde for 10 min at room temperature and mounted in Vectashield Mounting medium DAPI (Vector Laboratories, Peterborough, UK). Slides were examined with a Leica SP2 AOBS confocal microscope equipped with a 63×1.4 oil lens (Leica, Heidelberg, Germany). Excitation/emission settings for different fluorescent labels were as following: Alexa-488, excitation: 488 nm/detected emission: 503-585 nm; Alexa-594, excitation: 594 nm/detected emission: 611-689 nm and DAPI excitation: 405 nm, detected emission: 410-527 nm. All images were processed using Adobe Photoshop CS.

Measurement of Soluble Siglecs

Levels of soluble Siglec-5 and Siglec-9 were measured using enzyme linked immunosorbent assay (ELISA) kits according to the manufacturer's instructions (R&D Systems, Abingdon, UK). An in-house ELISA was developed to measure CD33. Immulon 4 ELISA plates (Dynatech, Chantilly, Va.) were coated overnight at 4° C. with purified 6C5 anti-CD33 mAb at 4 µg/ml in carbonate buffer pH 9.6, followed by either the test sample or a CD33 standard, comprising the CD33 extracellular region fused to enhanced green fluorescent protein. After 1 h at room temperature, wells were washed and incubated with affinity-purified rabbit anti-CD33, followed by goat anti-rabbit-horse radish peroxidase. ELISAs were developed using O-phenylamine diamine and absorbances measured at 450 inn. All samples were analysed in triplicate at 2 different dilutions in 2 independent assays.

Results

Characterisation of the Expression Pattern of the CD33-related Siglecs in AML.

To assay expression of the CD33-related siglecs on a collection of 21 cryopreserved AML cell samples, in-house generated anti-siglec mAbs were labelled with FITC and used at a saturating concentration as determined by staining of normal blood leukocytes. For each anti-siglec mAb, two-colour staining was performed using a biotinylated commercial anti-CD33 mAb detected with streptavidin-APC and samples analysed by flow cytometry (Table 2). As expected, 1-step staining with FITC-labelled anti-CD33 mAb gave lower levels of labelling compared with the 2-step staining, reflecting a generally lower sensitivity of directly labelled mAbs (Table 2). A large variation in the percentage of siglec-positive cells was observed, but each siglec was invariably expressed within the CD33+ subset of AML cells (FIG. 1). Using FITC-labelled mAbs and taking a percentage cut-off of 5%, 17 of 21 samples expressed CD33 (median %, 37; median MFI, 25), 12 expressed Siglec-5 (median %, 13.5; median MFI, 27.5), 11 expressed Siglec-9 (median % 25; median MFI, 37), 5 expressed Siglec-7 (median %, 28.5, median MFI, 22.5) and 2 expressed Siglec-10 (median % 10.4; median MFI, 21). No expression of Siglec-8 or Siglec-10 was seen on any sample analysed, and low levels of expression were seen for Siglec-6 in one case (Table 2). Apart from CD33, Siglec-9 was the most strongly expressed of the CD33-related siglecs, both in terms of the percentages of positive cells and the MFI values of the positive subsets. The analysis showed that in seven cases it was expressed on a similar or even higher percentage of AML cells than CD33 (Table 2). A representative sample (XXI, Table 2) in which several CD33-related siglecs were clearly detected on AML cells is shown in FIG. 1.

Myelomonoblastic (FAB: M4) and monoblastic (FAB: M5) AML cells showed an increased expression of Siglecs-5, -7, -9 and -10 when compared to AML cells with a more immature phenotype (FAB: M0, M1, M2) (Table 2). This result is consistent with earlier studies on expression of Siglec-5 and Siglec-7 on AML cells[17,18]. The expression of Siglecs-5, -7 and -9 on CD33-positive subsets of cells raised the possibility that these molecules were coexpressed on the same subset of AML cells rather than on separate subsets. This was confirmed for two different AML samples using multi-parameter flow cytometry (FIG. 2).

TABLE 2

Expression of the CD33-related siglecs on primary bone marrow AML cells.

| Sample | FAB | CD33 (2-step)* % | CD33 FITC % | CD33 FITC MFI | Siglec-5 FITC % | Siglec-5 FITC MFI | Siglec-6 (2-step)* % | Siglec-7 FITC % | Siglec-7 FITC MFI | Siglec-8 FITC % | Siglec-9 FITC % | Siglec-9 FITC MFI | Siglec-10 FITC % | Siglec-10 FITC MFI | Siglec-11 FITC % |
|---|---|---|---|---|---|---|---|---|---|---|---|---|---|---|---|
| I | M0/M1 | 98 | 59 | 22 | 5.0 | 15 | ND | 2.8 | 16 | (—) | 7.0 | 23 | (—) | — | (—) |
| II | M0/M1 | 84 | 2.3 | 27 | (—) | — | ND | (—) | — | (—) | 7.9 | 39 | (—) | — | (—) |
| III | M1 | 99 | 39 | 21 | (—) | — | ND | (—) | — | (—) | (—) | — | (—) | — | (—) |
| IV | M1 | 98 | 91 | 25 | 5.0 | 15 | ND | 0.6 | 16 | (—) | 1.0 | 15 | (—) | — | (—) |
| V | M1 | 15 | 1.1 | 15 | 0.6 | 19 | (—) | 1.0 | 17 | (—) | 1.1 | 38 | (—) | — | (—) |
| VI | M1 | 85 | 7.6 | 16 | 6.5 | 30 | (—) | 0.6 | 17 | (—) | 1.7 | 28 | (—) | — | (—) |
| VII | M1 | 1.1 | 0.8 | 44 | 6.5 | 50 | (—) | (—) | — | (—) | 0.6 | 41 | (—) | — | (—) |
| VIII | M1 | 92 | 48 | 31 | 8.8 | 28 | ND | ND | — | (—) | 12 | 39 | (—) | — | (—) |
| IX | M2 | 55 | 22 | 38 | 35 | 27 | 4† | 0.9 | 21 | (—) | 4.1 | 27 | (—) | — | (—) |
| X | M2 | 12 | 5.7 | 22 | 3.5 | 22 | (—) | (—) | — | (—) | 2.1 | 27 | (—) | — | (—) |
| XI | M2 | 79 | 68 | 17 | 1.0 | 12 | (—) | 1.2 | 12 | (—) | 0.6 | 17 | (—) | — | (—) |
| XII | M2 | 47 | 2.4 | 28 | 4.0 | 26 | ND | 2.1 | 30 | (—) | 1.7 | 32 | (—) | — | (—) |
| XIII | M4 | 70 | 37 | 25 | 14 | 23 | (—) | 2.8 | 20 | (—) | 43 | 44 | (—) | — | (—) |
| XIV | M4 | 84 | 70 | 44 | 80 | 34 | ND | 45 | 34 | (—) | 25 | 35 | 1.4 | 32 | (—) |
| XV | M4 | 86 | 17 | 16 | 9.5 | 17 | ND | (—) | — | (—) | 1.8 | 19 | 1.6 | 14 | (—) |
| XVI | M5 | 92 | 76 | 37 | 22 | 19 | ND | 31 | 22 | (—) | 53 | 26 | 1.5 | 26 | (—) |
| XVII | M5 | 89 | 23 | 21 | 36 | 31 | (—) | 26 | 23 | (—) | 38 | 55 | 13.4 | 20 | (—) |
| XVIII | M6 | 13 | 6.4 | 39 | 6.2 | 38 | ND | ND | — | (—) | 7.1 | 33 | ND | — | ND |
| XIX | ND | 44 | 50 | 26 | 42 | 18 | ND | 33 | 16 | (—) | 42 | 20 | 4.6 | 13 | (—) |
| XX | ND | 93 | 16 | 32 | 5.0 | 29 | ND | (—) | — | (—) | 17 | 37 | (—) | — | (—) |
| XXI | ND | 53 | 36 | 50 | 13 | 20 | ND | 23 | 30 | (—) | 33 | 75 | 7.4 | 22 | (—) |

FAB, French-American-British classification; MFI, median fluorescence intensity of positive subset;
(—), no siglec-positive cells detectable; —, not applicable; ND, not determined.
*2-step refers to staining carried out with biotinylated Ab followed by streptavidin-APC (CD33) or unlabelled Ab followed by labelling with anti-mouse-FITC (Siglec-6),
† MFI value was 26.

Immunophenotypic Properties and Colony Forming Potential of Siglec-9+ AML Cells

The relatively high expression of Siglec-9 in several cases of AML suggests that this siglec might serve as both a useful marker and a potential therapeutic target in certain subtypes of AML. To further characterise the Siglec-9$^+$ AML subsets, additional phenotypic analyses were carried out, demonstrating that the majority of Siglec-9$^+$ cells were CD38$^-$, CD123$^{+/-}$, CD117$^+$ and CD14$^+$ (FIG. 3A). In addition, CD33$^+$ and Siglec-9$^+$ cells were compared for the expression of CD34 (class II) which is known to be expressed on leukemic stem cells (LSC)[20]. The result showed that in 8 of 10 samples analysed, only very few Siglec-9$^+$ cells expressed CD34, unlike CD33, which was detected on a higher percentage of CD34$^+$ cells (FIG. 3B). Taken together, the immunophenotype of Siglec-9$^+$ cells was consistent with monocytic cells. This was confirmed by May-Grunwald-Giemsa staining of sorted Siglec-9$^+$ and Siglec-9$^-$ AML cells (FIG. 4A).

Although the majority of Siglec-9$^+$ cells lacked expression of CD34 (FIG. 3B) the few Siglec-9$^+$/CD34$^+$ cells could include leukemic cells with blast colony forming potential[19]. To investigate this possibility Siglec-9$^+$ and Siglec-9$^-$ AML cells were purified by FACS sorting and CFU-blast assays in methylcellulose performed for three different AML samples. In all cases, no CFU-blast were detected within the Siglec-9+ fractions, whereas the Siglec-9$^-$ fractions had 2, 200 and 238 CFU-blast colony initiating cells per 10$^5$ cells in the three patients' samples analysed. Control experiments with unsorted cells incubated with or without anti-Siglec-9 mAb showed that there was no effect of the mAb on CFU-blast formation (data not shown).

Characterisation of CD33-related Siglec Expression on Normal Bone Marrow Cells

Apart from CD33 and Siglec-5, there have been no detailed reports on the expression profiles of the CD33-related Siglec family on normal bone marrow cells. This is important in the context of Ab-mediated targeting of AML cells in which it would be desirable to spare normal progenitor cells from cytotoxic effects. Three subpopulations of normal bone marrow cells were defined by flow cytometry according to side scatter (SSC) properties, respectively SSC$^{low}$ (FIG. 5, R2), SSC$^{medium}$ (FIG. 5, R3) and SSC$^{high}$ (FIG. 5, R4)[21]. In four normal bone marrow samples analysed, the expression of the CD33-related Siglecs was mostly confined to the SSC$^{medium}$ and SSC$^{high}$ populations and a representative example is shown in FIG. 5. The majority of SSC$^{medium}$ cells were strongly positive for CD33 and Siglec-9 and weakly positive for Siglecs-5 and -7. In comparison, the SSC$^{high}$ cells were weakly positive for CD33 and Siglec-5, but mostly negative for Siglec-9 (FIG. 5). Multicolour labeling showed that the SSC$^{medium}$, CD33$^{high}$, Siglec-9$^+$ subpopulation (FIG. 6A, gate 1) also co-expressed Siglecs-5 and -7. In contrast, the SSC$^{high}$, CD33$^{low}$, Siglec-9$^+$, (FIG. 6A, gate 2) cells were only positive for Siglec-5, but negative for Siglec-7. The Siglec-9$^+$ subpopulation was further defined as CD38$^-$, CD123$^{+/-}$, CD14$^+$ and CD34$^-$ (FIGS. 6B, C). Taken together with May Grunwald Giemsa staining of purified Siglec-9$^+$ cells (FIG. 4B), these results indicate that Siglec-9+ cells in normal bone marrow are predominantly immature cells of the monocytic lineage. Examination of CD34$^+$ cells showed that, similar to Siglec-9, Siglec-7 was mostly absent whereas Siglec-5 was detected on ~5% and CD33 on ~14% of CD34$^+$ cells (FIG. 6C). Myeloid progenitor cells characteristically express CD34 and CD33. Although the majority of Siglec-9$^+$ cells in normal marrow were CD34$^-$CD33$^+$, a small fraction (~1%) of the CD34$^+$ cells were Siglec-9$^+$ (FIG. 6C). To investigate whether a subset of progenitors expressed Siglec-9, normal bone marrow cells were sorted into Siglec-9$^+$ and Siglec-9$^-$ cell fractions by flow cytometry and their colony forming ability was measured using a standard methylcellulose-based clonogenic assay. Two independent experiments showed that the Siglec-9$^+$ cell fraction contained no colony forming cells, in contrast to the negative fraction, which contained the expected levels of BFU-E, CFU-E, CFU-G and CFU-GM cells (Table 3).

TABLE 3

Quantification of bone marrow colony forming cells in Siglec-9-negative and Siglec-9-positive cell fractions after cell sorting.

| Cell fractions | CFU-E | BFU-E | CFU-G | CFU-M | CFU-GM | CFU-GEMM |
|---|---|---|---|---|---|---|
| Unsorted BM, No mAb incubation | 4.5* [4, 5] | 5.5 [4, 7] | 26 [31, 21] | 11 [13, 9] | 14.5 [19, 9] | 0 [0, 0] |
| Unsorted BM, MAb incubation | 2 [2, 2] | 1.5 [0, 3] | 38 [41, 35] | 6 [6, 6] | 18.5 [18, 19] | 0 [0, 0] |
| Siglec-9$^+$ fraction | 0 [0, 0] | 1 [2, 0] | 0 [0, 0] | 0 [0, 0] | 0 [0, 0] | 0 [0, 0] |
| Siglec-9$^-$ fraction | 10.5 [14, 7] | 15.5 [17, 14] | 88 [109, 67] | 19 [18, 20] | 25 [25, 25] | 1 [1, 1] |

BM, normal bone marrow; mAb, anti-Siglec-9 mAb.
*The data show the mean of duplicate colonies per well from 1 × 10$^4$ cells incubated for 14 days in methylcellulose medium supplemented with Stem Cell Factor, GM-CSF, G-CSF, IL-6, IL-3 and erythropoietin. The brackets show the individual counts for both duplicates. Similar results were obtained in two independent experiments using normal bone marrow from two different donors.

In conclusion, analysis of normal bone marrow showed that Siglecs-5, -7 and -9 are expressed on differentiating cells of the myeloid lineages. In the case of Siglec-9, this receptor is absent from myeloid progenitors in contrast to CD33. Overall, the phenotype of AML cells and primary bone marrow cells that express CD33-related siglecs are similar, suggesting that the CD33-related siglecs are not expressed aberrantly in AML.

Anti-Siglec-9 mAb is Rapidly Internalised by AML Cells and Siglec-9-transfected Rat Basophil Leukemia Cells The relatively high expression of Siglec-9 on monocytic AML cells and its absence from myeloid progenitors makes it a potential new candidate for mAb based therapy, aimed at ablating blast cells and lowering the leukemic cell burden in the patient via toxin delivery. For this to be effective, it would be essential that anti-Siglec-9 mAb is internalized upon binding to the cell surface. To analyse mAb internalization, a flow cytometric assay was developed in which cells were labelled with Alexa 488-labelled anti-Siglec-9 mAb on ice and then incubated for varying periods at 37° C. The amount of bound mAb remaining was then measured using APC-labelled anti-mouse Ig followed by flow cytometry. The results of three independent experiments with primary AML samples showed that 30-50% of bound anti-Siglec-9 mAb was internalized within 40 min at 37° C. and up to 90% was internalised by 240 min (FIG. 7A, left panel). The loss of surface anti-Siglec-9 mAb was due to internalization rather than shedding since the amount of cell-associated Alexa-488-labelled anti-Siglec-9 mAb remained constant during the time-course of the experiment (FIG. 7B, left panel). To demonstrate directly that Siglec-9 could mediate internalization of anti-Siglec-9 mAb and investigate the role of the two cytoplasmic tyrosine-based signalling motifs (Y1 and Y2),[15] we examined the internalization of anti-Siglec-9 Ab in Siglec-9 stably-transfected RBL cells by flow cytometry and confocal microscopy. Using a similar assay as described above for the AML cells, RBL cells expressing wild-type or Y2F (membrane distal tyrosine changed to phenylalanine) mutant Siglec-9 showed similar rates of endocytosis such that by 40 min, 40-50% of Siglec-9 was internalized (FIG. 7A, right panel). In comparison, the Siglec-9 Y1F (membrane proximal tyrosine changed to phenylalanine) mutant was internalized more slowly (FIG. 7A, right panel). The total cell-associated anti-Siglec-9-Alexa-488 appeared to increase slightly due to a gain in autofluoresence over the time-course of the experiment (FIG. 7B, right panel). Internalization by RBL was confirmed by confocal microscopy in which wild type or Y2F forms of Siglec-9 showed high levels of internalization after 1 h incubation, whereas the Siglec-9 Y1F mutant remained mostly at the cell surface (Data Supplement Figure). These experiments showed that the membrane proximal ITIM of Siglec-9 is required for optimal endocytosis and is consistent with previous studies on CD33[16].

Soluble Forms of Siglec-9 are Either Low or Undetectable in AML Bone Marrow Plasma Whereas Siglec-5 is Present at High Levels For an anti-Siglec-9 mAb to function effectively in targeting AML cells in vivo, it is important that high levels of soluble Siglec-9 are absent from plasma, since this might neutralise injected Ab and reduce therapeutic efficacy. Indeed, a high antigenic load of CD33 in blood may significantly affect the clinical outcome following Mylotarg treatment[22]. We therefore investigated the levels of soluble Siglec-9 in bone marrow plasma collected from eight AML patients, including several with M4/M5 FAB status and one patient (AP3, Table 4) shown to have high levels of Siglec-9+ AML cells (sample XIII, Table 2). We also measured soluble CD33 and Siglec-5 for comparison. Undetectable levels of soluble Siglec-9 (limit of detection 1.25 ng/ml) were present in plasma from six patients and very low levels (~4 ng/ml) were detected in two patients (Table 4). In comparison, low to intermediate levels (4-30 ng/ml) of soluble CD33 were seen in all patients and Siglec-5 was readily detectable in 7 of 8 patients examined, with levels up to ~500 ng/ml (Table 4). No Siglec-9 could be detected in normal bone marrow plasma or normal blood serum samples, whereas soluble Siglec-5 was seen in all but one. CD33 was detected in one of three normal bone marrow plasma samples and in all normal blood serum samples. In general, levels of Siglec-5 and CD33 were higher in the AML samples than controls and these correlated to some extent with the numbers of circulating blood leukocytes in each patient (Table 4).

TABLE 4

Levels of soluble Siglec-5 and Siglec-9 in bone marrow plasma from AML patients and controls.

| Sample | FAB | WBC cells/µl | CD33 ng/ml* | Siglec-5 ng/ml | Siglec-9 ng/ml |
|---|---|---|---|---|---|
| AP1 | M2 | 2.2 | 6.4 ± 1.3 | (—) | (—) |
| AP2 | RAEB | 2 | 3.2 ± 0.6 | 128 ± 12 | (—) |
| AP3 | M5A | 6 | 4.1 ± 0.9 | 318 ± 39 | (—) |
| AP4 | M2 | 14 | 0.4 ± 0.4 | 83 ± 2 | (—) |
| AP5† | M4 | 26 | 12.2 ± 0.4 | 451 ± 13 | (—) |
| AP6 | M5A | 107 | 26.1 ± 0.4 | 464 ± 44 | 4.3 ± 0.1 |
| AP7 | M5A | 407 | 12.9 ± 0.9 | 535 ± 95 | 4.7 ± 0.6 |
| AP8 | M2 | 160 | 29.6 ± 1.1 | 359 ± 14 | (—) |
| NP1 | — | ND | (—) | (—) | (—) |
| NP2 | — | ND | (—) | 72 ± 5 | (—) |
| NP3 | — | ND | 6 ± 0.8 | 57 ± 0 | (—) |
| NS1 | — | ND | 3.2 ± 0.2 | 104 ± 1 | (—) |
| NS2 | — | ND | 0.6 ± 0.2 | 69 ± 3 | (—) |
| NS3 | — | ND | 5.8 ± 0.2 | 54 ± 32 | (—) |

WBC, white blood cells; AP, AML bone marrow plasma; NP, normal bone marrow plasma; NS, normal blood serum; (—), not detected, — not relevant, ND, not determined. The data show mean ± one standard deviation, FAB, French-American-British classification.
†This sample corresponds to sample XIII in Table 2.

Discussion

In this paper we describe the first comprehensive analysis of CD33-related siglec expression in AML. The aim of this screen was to determine if there are additional CD33-related siglecs that could be used for clinical purposes, either as markers to monitor disease or as therapeutic targets. Apart from CD33, Siglec-9 stood out as an interesting new candidate and was shown to be present at similar levels to CD33 in 7 out of 21 AML cases analysed. We also compared the CD33-related siglecs for their expression profile on normal bone marrow cells and demonstrated that, in contrast to CD33, Siglec-9 is absent from myeloid progenitors but was present at similar levels to CD33 on immature cells of the monocytic lineage. Taken together with our demonstration that anti-Siglec-9 is rapidly internalised by AML cells and is not present in plasma at significant levels, these findings raise the possibility that anti-Siglec-9 antibodies could be exploited for therapeutic purposes in AML, either alone or in conjunction with other treatments, including anti-CD33 mAb-based therapy.

A characteristic feature of the CD33-related siglecs is their lineage-restricted expression pattern. For example, Siglecs-5 and -9 are mostly found on monocytes and neutrophils[6, 11, 23, 24] Siglec-7 is predominantly expressed on monocytes and NK cells[7], Siglec-8 is restricted to eosinophils[9, 10] and Siglec-11 is expressed in tissue macrophages but is absent from circulating leukocytes[13]. This differential staining on normal blood leukocytes is consistent with the pattern of expression observed here using a diverse collection of AML samples ranging in FAB classification from M0 to M6. Thus, Siglecs-8 and -11 were not detectable on any leukemic samples analysed whereas Siglecs-5, -7, and -9 were variably present on most samples. From side-by-side comparisons of all CD33-related siglecs, it is clear that CD33 is expressed at high levels on the majority of AML samples irrespective of FAB status, (consistent with many previous studies), whereas the other CD33-related siglecs are only expressed at significant levels on subsets of CD33+ AML cells with features of myelomonocytic differentiation. An important question from a therapeutic perspective is whether Siglecs-5, -7 and -9 are expressed on the same or on separate subsets of AML cells. We demonstrated here by multiparameter labelling that all 3 siglecs were co-expressed on the same subsets, consistent with the notion that expression of these molecules is co-ordinately regulated during AML cell differentiation.

In this study, we showed that Siglec-9 was absent from all progenitors assayed, including CFU-G, CFU-M and CFU-GM and our observations, suggest that Siglecs-5 and -7 are also absent from myeloid progenitors. Therefore, it is likely that Siglecs-5, -7 and -9 are first expressed on CD33[+] cells of the myelomonocytic lineages once they have lost the ability to form colonies in response to growth factors. Interestingly, expression of Siglec-9 on immature bone marrow neutrophils (defined by high side-scatter, FIG. 5) was weak or absent, suggesting that Siglec-9 is upregulated on these cells following their exit from the marrow. In contrast, CD33 is readily detectable on immature neutrophils and is downregulated on maturation.

The LSC is currently considered as a key target for treatment of AML[1, 25] and is found within the CD34[+]CD38[-] population[20, 26]. The absence of Siglec-9 from myeloid progenitors suggests that it is also likely to be absent from LSCs. Consistent with this possibility, we demonstrated that cells sorted on the basis of Siglec-9 expression did not include any AML blast colony forming cells. Therefore it is unlikely that anti-Siglec-9 mAb used alone would be capable of directly ablating the LSCs, but may be effective in targeting radioisotopes to the bone marrow for bystander toxicity to these rare cells. Anti-Siglec-9 mAb may also be useful in conjunction with anti-CD33 Abs or other therapies, for example in reducing the leukemic burden in certain cases of myelomonoblastic leukemia.

There are several potential advantages of targeting Siglec-9 for this purpose compared with Siglec-5 and Siglec-7. First, Siglec-9 had the highest expression levels as revealed by MFI values (Table 1 and FIG. 1), This, combined with the rapid uptake of bound Ab shown here, would be expected to lead to high levels of endocytosed Ab conjugates into leukemic cells, resulting in efficient cell death. Second, concentrations of soluble Siglec-9 in bone marrow plasma from AML patients and controls was low or undetectable, whereas Siglec-5 was present at high concentrations and could possibly neutralise a significant fraction of injected Ab. The analysis of soluble CD33 showed significant levels of this molecule also, and the elevation of both CD33 and Siglec-5 in AML samples clearly correlated with the number of circulating white blood cells in each patient. This suggests that the increased pool of soluble siglecs is leukemia cell-derived. Although the molecular properties of soluble siglecs are currently unknown, a previous report described the existence of multiple splice variants of Siglec-5, including one encoding a soluble, secreted form[24].

In conclusion, our findings demonstrate that Siglec-9 is expressed on (myelo)monoblastic leukemias and provides a potential novel therapeutic target, especially if considered as a tailored therapy, used in conjunction with conventional cytotoxic agents or novel agents including anti-CD33 directed strategies.

References

1. Jordan C T, Guzman M L. Mechanisms controlling pathogenesis and survival of leukemic stem cells. Oncogene. 2004; 23:7178-7187.
2. Bennett J M, Catovsky D, Daniel M T, Flandrin G, Galton D A, Gralnick H R, Sultan C. Proposals for the classification of the acute leukaemias. French-American-British (FAB) co-operative group. Br J. Haematol. 1976; 33:451-458.
3. Bennett J M. World Health Organization classification of the acute leukemias and myelodysplastic syndrome. Int J Hematol. 2000; 72:131-133.
4. Varki A, Angata T. Siglecs—the Major Sub-family of I-type Lectins. Glycobiology. 2005.
5. Crocker P R. Siglecs in innate immunity. Curr Opin Pharmacol. 2005; 5:431-437,
6. Cornish A L, Freeman S, Forbes G, Ni J, Zhang M, Cepeda M, Gentz R, Augustus M, Carter K C, Crocker P R. Characterization of siglec-5, a novel glycoprotein expressed on myeloid cells related to CD33. Blood. 1998; 92:2123-2132.
7. Nicoll G, Ni J, Liu D, Klenerman P, Munday J, Dubock S, Mattei M G, Crocker P R. Identification and characterization of a novel siglec, siglec-7, expressed by human natural killer cells and monocytes. J Biol. Chem. 1999; 274: 34089-34095.
8. Patel N, Brinkman-Van der Linden E C, Altmann S W, Gish K, Balasubramanian S, Timans J C, Peterson D, Bell M P, Bazan J F, Varki A, Kastelein R A. OB-BP1/Siglec-6. a leptin- and sialic acid-binding protein of the immunoglobulin superfamily. J Biol Chem. 1999; 274:22729-22738.
9. Floyd H, Ni J, Cornish A L, Zeng Z, Liu D, Carter K C, Steel J, Crocker P R. Siglec-8. A novel eosinophil-specific member of the immunoglobulin superfamily. J Biol. Chem. 2000; 275:861-866.
10. Kikly K K, Bochner B S, Freeman S D, Tan K B, Gallagher K T, D'Alessio K J, Holmes S D, Abrahamson J A, Erickson-Miller C L, Murdock P R, Tachimoto H, Schleimer R P, White J R. Identification of SAF-2, a novel siglec expressed on eosinophils, mast cells, and basophils. J Allergy Clin Immunol. 2000; 105:1093-1100.
11. Zhang J Q, Nicoll G, Jones C, Crocker P R, Siglec-9, a novel sialic acid binding member of the immunoglobulin superfamily expressed broadly on human blood leukocytes. J Biol. Chem. 2000; 275:22121-22126.
12. Munday J, Kerr S, Ni J, Cornish A L, Zhang J Q, Nicoll G, Floyd H, Mattei M G, Moore P, Liu D, Crocker P R. Identification, characterization and leucocyte expression of Siglec-10, a novel human sialic acid-binding receptor. Biochem J. 2001; 355:489-497.
13. Angata T, Kerr S C, Greaves D R, Varki N M, Crocker P R, Varki A. Cloning and characterization of human Siglec-11. A recently evolved signaling that can interact with SHP-1 and SHP-2 and is expressed by tissue macrophages, including brain microglia. J Biol. Chem. 2002; 277:24466-24474.
14. Lock K, Zhang J, Lu J, Lee S H, Crocker P R. Expression of CD33-related siglecs on human mononuclear phagocytes, monocyte-derived dendritic cells and plasmacytoid dendritic cells. Immunobiology. 2004; 209:199-207.
15. Avril T, Floyd H, Lopez F, Vivier E, Crocker P R. The membrane-proximal immunoreceptor tyrosine-based inhibitory motif is critical for the inhibitory signaling mediated by Siglecs-7 and -9, CD33-related Siglecs expressed on human monocytes and NK cells. J. Immunol. 2004; 173:6841-6849.
16. Walter R B, Raden B W, Kamikura D M, Cooper J A, Bernstein I D. Influence of CD33 expression levels and ITIM-dependent internalization on gemtuzumab ozogamicininduced cytotoxicity. Blood. 2005; 105:1295-1302.
17. Virgo P, Denning-Kendall P A, Erickson-Miller C L, Singha S, Evely R, Hows J M, Freeman S D. Identification of the CD33-related Siglec receptor, Siglec-5 (CD170), as a useful marker in both normal myelopoiesis and acute myeloid leukaemias. Br J Haematol, 2003; 123:420-430.
18. Vitale C, Romagnani C, Puccetti A, Olive D, Costello R, Chiossone L, Pitto A, Bacigalupo A, Moretta L, Mingari M C. Surface expression and function of p75/AIRM-1 or CD33 in acute myeloid leukemias: engagement of CD33 induces apoptosis of leukemic cells. Proc Natl Acad Sci USA. 2001; 98:5764-5769.
19. Blair A, Hogge D E, Ailles L E, Lansdorp P M, Sutherland H J. Lack of expression of Thy-1 (CD90) on acute myeloid leukemia cells with long-term proliferative ability in vitro and in vivo. Blood. 1997; 89:3104-3112.
20. Lapidot T, Sirard C, Vormoor J, Murdoch B, Hoang T, Caceres-Cortes J, Minden M, Paterson B, Caligiuri M A, Dick J E. A cell initiating human acute myeloid leukaemia after transplantation into SCID mice. Nature. 1994; 367: 645-648,
21. Andrews R G, Singer J W, Bernstein I D. Precursors of colony-forming cells in humans can be distinguished from colony-forming cells by expression of the CD33 and CD34 antigens and light scatter properties. J Exp Med. 1989; 169:1721-1731.
22. van der Velden V H, Boeckx N, Jedema I, to Marvelde J G, Hoogeveen P G, Boogaerts M, van Dongen J J, High CD33-antigen loads in peripheral blood limit the efficacy of gemtuzuniab ozogamicin (Mylotarg) treatment in acute myeloid leukemia patients. Leukemia. 2004; 18:983-988.
23. Angata T, Varki A. Cloning, characterization, and phylogenetic analysis of siglec-9, a new member of the CD33-related group of siglecs. Evidence for co-evolution with sialic acid synthesis pathways. J Biol. Chem. 2000; 275: 22127-22135.
24. Connolly N P, Jones M, Watt S M. Human Siglec-5: tissue distribution, novel isoforms and domain specificities for sialic acid-dependent ligand interactions. Br J Haematol. 2002; 119:221-238.
25. Sperr W R, Hauswirth A W, Florian S, Ohler L, Geissler K, Valent P. Human leukaemic stem cells: a novel target of therapy. Eur J Clin Invest. 2004; 34 Suppl 2:31-40.
26. Hope K J, Jin L, Dick J E. Acute myeloid leukemia originates from a hierarchy of leukemic stem cell classes that differ in self-renewal capacity. Nat. Immunol. 2004; 5:738-743.
27. Parishi, E., Draznin, J., Stoopler, E., Schuster, S. J., Poreter, D. and Sollecito, T. P. Acute myelogenous leukaemia: advances and limitations of treatment. oral Surg Oral Med Oral Pathol oral Radiol Endod 2002; 93, 257-263.

The invention claimed is:
1. A method of treating a subject having a Siglec-9-expressing cell proliferation and/or differentiation disorder comprising administering to said subject an effective amount of an anti-Siglec-9 antibody comprising a cytotoxic agent.
2. The method of claim 1, wherein the Siglec-9-expressing cell proliferation and/or differentiation disorder affects cells of the immune system and/or cells of the bone marrow.
3. The method of claim 1 or 2, wherein the Siglec-9-expressing cell proliferation and/or differentiation disorder is cancer.
4. The method of claim 3, wherein the cancer is a malignant disorder of the monocytic, macrophage and/or histiocytic lineages and/or acute myeloid leukemia (AML).
5. The method of claim 1, wherein the Siglec-9-expressing cell proliferation and/or differentiation disorder is Acute myeloid leukemia (AML) with inv(16)(p13q22).
6. The method of claim 1, wherein the anti-Siglec-9 antibody agent is a polyclonal antibody or a monoclonal antibody which specifically binds to Siglec-9.
7. The method of claim 6, wherein the antibody does not induce complement mediated or antibody dependant cellular cytotoxicity (ADCC).
8. The method of claim 7, wherein the antibody is derived from a heterologous species.
9. The method of claim 8, wherein the antibody is a human or humanized antibody.
10. The method of claim 1, wherein the antibody is an antibody fragment selected from the group consisting of:
    (i) F(ab)$_2$ fragments
    (ii) Fab fragments; and
    (iii) domain antibodies (nanobodies).
11. The method of claim 1, wherein the anti-Siglec-9 antibody the activity of Siglec-9 and/or the proliferative and/or differentiative state of a cell.
12. The method of claim 1, wherein the anti-Siglec-9 antibody, once bound, is internalized such that the anti-Siglec-9 antibody is delivered to the interior of a cell or to a compartment or vesicle within the cell.
13. The method of claim 1, wherein the cytotoxic agent is selected from the group consisting of:
    (a) a toxic substance,
    (b) a heavy metal; and
    (c) a toxin or toxoid.

* * * * *